Figure 1:
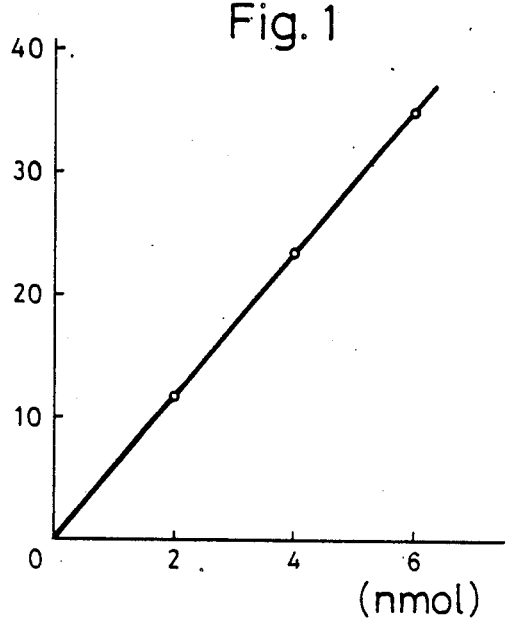

United States Patent [19]

Terada et al.

[11] Patent Number: 4,657,856
[45] Date of Patent: Apr. 14, 1987

[54] GLUTATHIONE PEROXIDASE, PROCESS FOR PRODUCTION THEREOF, METHOD AND COMPOSITION FOR THE QUANTITATIVE DETERMINATION OF LIPID PEROXIDE

[75] Inventors: Osamu Terada; Kazuo Aisaka, both of Machida, Japan

[73] Assignee: Kyowa Hakko Kogyo Co., Ltd., Tokyo, Japan

[21] Appl. No.: 303,137

[22] Filed: Sep. 17, 1981

[30] Foreign Application Priority Data

Sep. 25, 1980 [JP] Japan ................................ 55-132301

[51] Int. Cl.$^4$ .................... C12Q 1/28; C12Q 1/32; C12N 9/08; C12R 1/785

[52] U.S. Cl. ........................................ 435/28; 435/26; 435/192; 435/931

[58] Field of Search .................... 435/25, 28, 192, 810, 435/931, 26

[56] References Cited

PUBLICATIONS

Grosch et al, Chemical Abstracts, 78: 120,737c, 166 (1973).
Heath et al, Anal. Biochem., 76, 184–191 (1976).
Hissin et al, Anal. Biochem., 74, 214–226 (1976).

*Primary Examiner*—Esther M. Kepplinger
*Attorney, Agent, or Firm*—Antonelli, Terry & Wands

[57] ABSTRACT

Glutathione peroxidase is produced by fermentation of a microorganism of the genus Mucor. This peroxidase may be used for the determination of lipid peroxide.

8 Claims, 3 Drawing Figures

GLUTATHIONE PEROXIDASE, PROCESS FOR PRODUCTION THEREOF, METHOD AND COMPOSITION FOR THE QUANTITATIVE DETERMINATION OF LIPID PEROXIDE

This invention relates to glutathione peroxidase and a process for production thereof, and a method and composition for the quantitative determination of lipid peroxide. More particularly, this invention relates to glutathione peroxidase derived from a microorganism and not containing selenium and a process for production thereof which comprises culturing a microorganism belonging to the genus Mucor and capable of producing glutathione peroxidase in a culture medium, producing and accumulating glutathione peroxidase in the culture liquor and recovering the same therefrom. *Mucor hiemalis* YR-0929 (FERM BP-50) and *Mucor rouxianus* YR-0319 (FERM BP-51) were deposited on Sept. 22, 1980 outside the Budapest Treaty with the Fermentation Research Institute, Agency of Industrial Science and Technology, Japan. The deposits were converted into the deposits under the Budapest Treaty on May 1, 1981, and are available therefrom under the terms of the Budapest Treaty. *Mucor circinelloides* ATCC 15242 was deposited on Nov. 19, 1964 with the American Type Culture Collection, Rockville, Md., and is available therefrom.

Further, this invention relates to a method and a composition for the quantitative determination of lipid peroxide by the use of this glutathione peroxidase.

Glutathione peroxidase (EC 1.11.1.9) was first reported by Mills to be present in bovine erythrocytes (G. C. Mills; J. Biol. Chem., 229, 189 (1957)), and later it was reported that this is also present in the organs such as a liver, etc. (G. C. Mills; Arch. Biochem. Biophys. 86, 1 (1960)).

Further, it was reported that a glutathione peroxidase derived from an animal contains selenium (R. A. Sunde and W. G. Hoekstra; Nutrition Reviews, 38, 265 (1980)).

However, there has heretofore been no report on glutathione peroxidase derived from microorganisms.

Further, it is well known that glutathione peroxidase is used for the quantitative analysis of lipid peroxide (R. L. Heath and Al L. Tappel; Anal. Biochem., 76, 184 (1976)), and a process for production of glutathione peroxidase on an industrial scale is in demand.

The present inventors have studied various processes for production of glutathione peroxidase to find that when a microorganism belonging to the genus Mucor is cultured in a culture medium, glutathione peroxidase not containing selenium is produced in a remarkably large amount in the culture liquor, mostly in the microbial cells. Further, the present inventors have found a method and a composition for the quantitative determination of lipid peroxide, and have thus accomplished this invention.

This invention is described in detail below.

The microorganism to be used in this invention may be any strain as long as it belongs to the genus Mucor and is capable of producing glutathione peroxidase. Examples of the presently preferred strains are *Mucor hiemalis* YR-0929 (FERM BP-50), *Mucor circinelloides* (*Mucor javanicus*) ATCC 15242 and *Mucor rouxianus* YR-0319 (FERM BP-51).

The mycological properties of the genus to which these fungi belong are described in the following literature: A Manual of Soil Fungi, the 2nd Edition (1957); *Mucor hiemalis* on p. 38, *Mucor circinelloides* (*Mucor javanicus*) on p. 33 and *Mucor rouxianus* on p. 33, respectively.

Either a synthetic or natural medium may be used as long as it properly contains a carbon source, a nitrogen source, minerals and other nutrients.

As the carbon source, various carbohydrates such as glucose, fructose, sucrose, maltose, mannose, starch, starch hydrolyzate liquor, molasses, etc., various sugar alcohols such as glycerol, sorbitol, mannitol, etc., various organic acids such as acetic acid, lactic acid, pyruvic acid, fumalic acid, citric acid, etc., various alcohols such as methanol, ethanol, etc., various glycols such as ethylene glycol, propylene glycol, etc., various amino acids, and hydrocarbons such as n-hexadecane, etc., may be used.

As the nitrogen source, there may be employed ammonia, various inorganic and organic ammonium salts such as ammonium chloride, ammonium carbonate, ammonium phosphate, ammonium nitrate, ammonium acetate, etc., urea, amino acids and other nitrogen-containing compounds, as well as nitrogenous organic materials such as peptone, NZ-amine, meat extract, corn steep liquor, casein hydrolyzate, chrysalis hydrolyzate, fish meal, its digest product, defatted soybean, its digest product, etc.

As the minerals, appropriate are potassium primary phosphate, potassium secondary phosphate, potassium chloride, magnesium sulfate, manganese sulfate, ferrous sulfate, sodium chloride, calcium carbonate, etc.

Culturing is carried out with aerating and stirring at a pH of 6.0–7.0 and at a temperature of 25°–35° C. for 4–5 days.

Culturing is continued until glutathione peroxidase is produced and accumulated in the culture liquor, mostly in the microbial cells. Recovering of glutathione peroxidase from the culture liquor is carried out as follows:

After completion of culturing, and microbial cells are collected from the culture liquor by centrifugation, etc., then disrupting these microbial cells by suitable means, such as ultrasonic disintegration, grinding, mechanical pressure and autolysis to obtain the supernatant from the disrupted liquor by centrifugation.

The supernatant is subjected to a conventional treatment for enzyme purification, for example, salting-out, precipitation with organic solvent, dialysis, ion exchange cellulose column chromatography, Sephadex column chromatography, freeze-drying, etc. Thus, purified glutathione peroxidase can be recovered.

Properties of the enzyme obtained by this invention are now described with particular reference to glutathione peroxidase produced from *Mucor hiemalis* YR-0929 as the representative, glutathione peroxidases produced from *Mucor circinelloides* ATCC 15424 and *Mucor rouxianus* YR-0319 also have similar properties.

The enzymatic activity of glutathione peroxidase is calculated by reacting oxidized gluthathione produced by the enzyme with NADPH in the presence of glutathione reductase and measuring the decreasing rate of the absorbancy of NADPH at 340 nm on a spectrophotometer.

The reaction is illustrated by the following formulae (1) and (2):

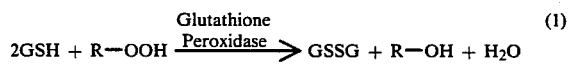

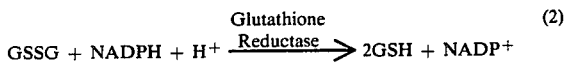

$$\text{GSSG} + \text{NADPH} + \text{H}^+ \xrightarrow{\text{Glutathione Reductase}} 2\text{GSH} + \text{NADP}^+ \quad (2)$$

wherein GSSG represents oxidized glutathione, NADPH represents reduced nicotinamide adenine dinucleotide phosphate dehydrogenase and NADP represents nicotinamide adenine dinucleotide phosphate.

(A) Reagents
(1) Substrate: 30 mM Cumene hydroperoxide aqueous solution: 0.2 ml
(2) Buffer: 100 mM Phosphate buffer (pH 7.0) containing 4 mM EDTA: 1.5 ml
(3) Reduced glutathione: 10 mM Aqueous solution: 0.3 ml
(4) Sodium azide: 10 mM Aqueous solution: 0.3 ml
(5) NADPH*: 1.6 mM Aqueous solution: 0.3 ml
(6) Glutathione reductase solution: Prepared by diluting with 100 mM phosphate buffer (pH 7.0) to 1 u/ml: 0.3 ml
(7) Enzyme solution: 0.1 ml
*Reduced nicotinamide adenine dinucleotide phosphate dehydrogenase (B) Operations The above reagents (1)–(6) are taken into a cuvette (d=1.0 cm) and preheated at 25° C. for 5 minutes. Thereafter, the enzyme solution is added thereto, the absorbancy at 340 nm is recorded at 25° C. for 2–3 minutes, and the change in absorbancy per minute is determined ($\Delta$OD test) from the linear section. On the other hand, as the control, the same solution as described above except that water instead of the substrate is used, is subjected to operations similar to the above and the change in absorbancy is determined ($\Delta$OD blank).

(C) Calculation of the titer

One unit of glutathione peroxidase is defined as the amount of the enzyme which oxidizes one $\mu$ mole of reduced glutathione (GSH) or oxidizes 0.5 $\mu$mole of NADPH per minute at 25° C. Since it has been reported that the extinction coefficient of 1 mM of NADPH is 6.22 (The Merck Index, 9th Edition, p. 824), the titer (A) per ml of the enzyme solution can be calculated from:

$$A = \frac{(\Delta OD \text{ test} - \Delta OD \text{ blank}) \times 3}{6.22 \times \frac{1}{2} \times 0.1}$$

$$= (\Delta OD \text{ test} - \Delta OD \text{ blank}) \times 9.65 \text{ (unit/ml)}.$$

Properties of glutathione peroxidase obtained in this invention are as follows:

(1) Action

This enzyme catalyzes the reaction wherein a hydroperoxide is reduced in the presence of reduced glutathione to produce the corresponding alcohol and oxidized glutathione.

(2) Substrate specificity

This enzyme acts upon cumene hydroperoxide, t-butyl hydroperoxide, linolenic acid hydroperoxide, etc.

| Substrate | Relative Activity (%) |
|---|---|
| Cumene hydroperoxide | 100 |
| t-Butyl hydroperoxide | 175 |
| Linolenic acid hydroperoxide | 98 |

(3) Optimum pH

The optimum pH for this enzyme is in the vicinity of pH 6.0–7.0 in the reaction at 25° C. for one minute.

(4) Stable pH range

The stable pH region for this enzyme is between pH 6.0 and 8.0 in the case of treatment at 4° for 20 hours.

(5) Range of temperatures suitable for action

The optimum temperature for this enzyme is in the vicinity of 30°–35° C. in the reaction at pH 7.0 for one minute.

(6) Temperature stability

This enzyme is stable up to 37° C. and loses about 80% of its activity at 45° C. with treatment at pH 6.0 for 10 minutes.

(7) Inhibition

When reacted at 25° C. and pH 7.0, this enzymatic action is inhibited by the following substances.

| Inhibiting Substance | Concentration (M) | Percent Inhibition (%) |
|---|---|---|
| PCMB* | $10^{-4}$ | 75 |
| " | $10^{-3}$ | 99 |
| N—Ethylmaleimide | $10^{-4}$ | 3 |
| " | $10^{-3}$ | 93 |
| Iodoacetamide | $10^{-4}$ | 1 |
| " | $10^{-3}$ | 16 |

*PCMB = Parachloromercurybenzoate (8) Molecular weight

The molecular weight of this enzyme is calculated to be about 55,000 by Sepharose CL-4B gel permeation method.

(9) Crystal structure and elementary analysis

These are not measured because this enzyme is not crystallized.

(10) Cofactor

X-rays fluorescent analyzer shows that there is no detectable amount of selenium of this enzyme.

(11) Sedimentation coefficient

The sedimentation coefficient of this enzyme, as measured by a ultracentrifuge, is $S_{20,w} = 2.24S$.

(12) Isoelectric point

The isoelectric point of this enzyme, as measured in the isoelectric cataphoresis analysis using ampholine, is pH 5.20.

(13) Amino acid analysis

The values of various amino acids contained in this enzyme are shown below, compared with glutathione peroxidase derived from a rat liver.

| Amino acid | The present enzyme | Glutathione peroxidase derived from a rat liver[a] |
|---|---|---|
| Lysine | 31[b] | 22[b] |
| Histidine | 8 | 8 |
| Arginine | 6 | 14 |
| Aspartic acid | 47 | 28 |
| Threonine | 21 | 16 |
| Serine | 22 | 18 |
| Glutamic acid | 38 | 30 |
| Proline | 23 | 20 |
| Glycine | 22 | 26 |

-continued

| Amino acid | The present enzyme | Glutathione peroxidase derived from a rat liver[a] |
|---|---|---|
| Alanine | 26 | 20 |
| Cystine | —[c] | 4 |
| Valine | 23 | 22 |
| Methionine | 0 | 6 |
| Isoleucine | 14 | 16 |
| Leucine | 36 | 30 |
| Tyrosine | 4 | 10 |
| Phenylalamine | 19 | 14 |
| Tryptophan | —[c] | 2 |

Note:
[a]Biochem. Biophys. Acta, 358, 251 ('74)
[b]The number of an amino acid residue contained in one molecule of the enzyme.
[c]not detectable.

The method for determination of a lipid peroxide using glutathione peroxidase will now be described.

In recent years, the determination of the amount of a lipid peroxide in the serum is very useful for diagnostic purposes in the determination of various diseases such as arteriosclerosis and diabetes. An enzymatic method for determination of a lipid peroxide using glutathione peroxidase derived from animal tissues is known (R. L. Heath and Al L. Tappel, Anal. Biochem., 76, 184 (1976)). This method, however, is not suitable for determination of a lipid peroxide in a living sample such as serum which contains many substances interfering with the determination, for example reducible substances.

The present inventors have found that the determination of a lipid peroxide can be performed with simplicity by combining a process for production of oxidized glutathione using glutathione peroxidase derived from a microorganism and the method for micro-determination of oxidized glutathione (P. J. Hissin and R. Hilf; Anal. Biochem., 74, 214 (1976)).

The present method for determination of a lipid peroxide is schematically shown below.

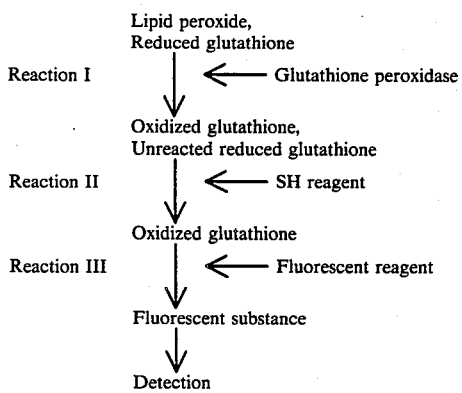

The above reactions are described in detail below.

(REACTION I)

A lipid peroxide, reduced glutathione, and glutathione peroxidase are added to a buffer solution (pH 5–7) and the reaction is carried out to convert reduced glutathione in an amount corresponding to the lipid peroxide into oxidized glutathione.

Any lipid peroxide may be used so long as it is a substrate for glutathione peroxidase. Specific examples include cumene hydroperoxide, t-butyl hydroperoxide, linolenic acid hydroperoxide, linoleic acid hydroperoxide, cholesterol hydroperoxide, arachidonic acid hydroperoxide, progesterone hydroperoxide, allopregnanolone hydroperoxide and pregnenolone hydroperoxide.

The glutathione peroxidase and reduced glutathione are used in an amount of 0.5 to 2.0 U, and 10 to 100 nanomoles (hereinafter referred to as "n moles"), respectively, per 1 to 10 n moles of the lipid peroxide.

The buffer solution may be a phosphate buffer solution, a Tris-HCl buffer solution, etc.

The reaction is usually carried out at 25° to 35° C. for 10 to 30 minutes.

The living sample may be prepared in a conventional manner. If the living sample contains substances which inhibit the action of glutathione peroxidase and/or substances which hinder fluorescent measurement of oxidized glutathione, it is subjected to pretreatment such as precipitation, ion-exchange chromatography and adsorption chromatography to remove the substances. Where a certain specified type of lipid peroxide is measured as an object, it is necessary to separate the certain lipid peroxide from lipid peroxides. A suitable method for the separation is selected depending upon the properties of the lipid peroxide to be separated, preferably chromatographic separation is employed.

(REACTION II)

After the enzymatic reaction, an SH reagent is added to the reaction mixture to undergo an addition reaction of the SH reagent with the unreacted reduced glutathione, whereby a free mercapto group of the reduced glutathione is blocked.

The SH reagent used may be any compound so long as it is easily reacted with reduced glutathione, has no reactivity with both oxidized glutathione and a fluorescent reagent, is ready to be destroyed to an alkali, and is non-fluorescent. Specific examples of the SH reagent are N-ethyl-maleimide, p-chloromercurybenzoate and iodoacetic acid.

The addition-reaction conditions may be determined depending upon the type of the SH reagent used.

The concentration of the SH reagent, which varies with the reduced glutathione used in the enzymatic reaction (Reaction I), may be 5 to 10 μmoles.

(REACTION III)

The resulting oxidized glutathione is reacted with a fluorescent reagent in the presence of an alkali to obtain a fluorescent substance.

An example of the fluorescent reagent is o-phthalaldehyde. The fluorescent reagent is preferably used in a concentration of 1 to 10 μmoles.

Sodium hydroxide, potassium hydroxide, etc., are used as the alkali. The preferred concentration of the alkali is 100 to 500 μmoles.

The reaction is usually carried out at 25° to 35° C. for 15 to 30 minutes.

The fluorescent substance produced is fluorometrically measured by a spectrofluorometer. In measuring an obtained fluorescent substance by a spectrofluorometer, an exciting wavelength and a measuring wavelength are appropriately selected depending on the kind of fluorescent reagent. In case o-phthalaldehyde is used as a fluorescent reagent the exciting wavelength is 350 nm and the measuring wavelength is 420 nm.

The present invention also provides a composition for determining a substrate for glutathione peroxidase.

The composition comprising (A) 0.5 to 2.0 U of glutathione peroxidase derived from a microorganism and 10 to 100 n moles of reduced glutathione, (B) 5 to 50

μmoles of an SH reagent, and (C) 1 to 10 μmoles of a fluorescent reagent and 100 to 500 μmoles of an alkali is exemplified.

This invention is specifically embodied in the following examples.

EXAMPLE 1

*Mucor hiemalis* YR-0929 (FERM BP-50) is inoculated into 300 ml of a culture medium (pH 6.0) comprising 1 g/dl glucose, 0.3 g/dl yeast extract and 0.3 g/dl malt extract in a 2 1-Erlenmeyer flask, and cultured with shaking at 30° C. for 48 hours.

Then, 600 ml of this culture liquor is transferred to a 30 1-jar fermenter containing 15 1 of a culture medium of the same composition and cultured with aerating and stirring (300 rpm) at 30° C. for 4 days.

Thereafter, 15 1 of this culture liquor is filtered through a large Nutsche funnel, to collect about 100 g (wet) of the microbial cells.

These microbial cells are washed with 5 1 of 0.01M phosphate buffer (pH 6.0) and suspended in 2 1 of the same buffer. This suspension is subjected to treatment using a DYNO MILL (product of Willy A. Bachofen Co., Switzerland) to grind the cells.

After grinding, the product is subjected to centrifugation (12,000 x g, 20 minutes) using a refrigerated centrifuge and the supernatant is recovered. A precipitate is obtained by treating the supernatant with ammonium sulfate of 50–90% saturation.

The yield in terms of activity of glutathione peroxidase contained in the precipitate is about 75%, and the specific activity thereof is elevated to threefold.

The precipitate is dissolved in about 100 ml of 0.01M phosphate buffer (pH 6.0) and the solution is dialyzed against 10 1 of the same buffer for 24 hours. The dialyzate is passed through a DEAE-cellulose column (1 1, 6 cm in inner diameter) equilibrated with the same buffer. In this procedure, glutathione peroxidase is adsorbed onto the DEAE-cellulose. Further, contaminated proteins are washed out with the same buffer as defined above.

Thereafter, elution is conducted with an eluent having a concentration gradient of from 0.01M phosphate buffer (pH 6.0) to 0.2M phosphate buffer (pH 6.0).

The active fraction of glutathione peroxidase is eluted as a single peak. This active fraction is collected and ammonium sulfate is added thereto, and the portion which is precipitated out with ammonium sulfate of 90% saturation is collected by centrifugation (12,000 x g, 20 minutes), and dissolved in 10 ml of 0.01M phosphate buffer (pH 6.0). This solution is dialyzed against 5 1 of the same buffer as defined above for 24 hours.

After dialysis, the enzyme solution is passed through a Sepharose CL-4B column (500 ml, 3.5 cm in inner diameter) equilibrated with the same buffer as defined above. The eluate is fractionated and recovered, the fractions exhibiting a high specific activity are collected and freezedried to obtain 50 mg of purified powdered glutathione peroxidase enzyme standard product (the specific activity of 15 unit/mg).

The purified enzyme exhibits a specific activity elevated to about 100 times as compared with the cell extract liquor, and the total yield in terms of activity is 50%.

EXAMPLE 2

Similar procedures to in Example 1 are performed except that the strain used is replaced by *Mucor circinelloides* ATCC 15242, to obtain about 40 mg of purified glutathione peroxidase having a specific activity of 12 unit/mg. The total yield in terms of activity is 50%.

EXAMPLE 3

Similar procedures to in Example 1 are performed except that the strain used in replaced by *Mucor rouxianus* YR-0319 (FERM BP-51), to obtain about 25 mg of purified glutathione peroxidase having a specific activity of 10 unit/mg. The total yield in terms of activity is 40%.

EXAMPLE 4

To a mixed solution consisting of 0.1 ml of a solution containing 20.8 unit/ml glutathione peroxidase obtained in Example 1, 0.5 ml of 100 mM phosphate buffer (pH 6.0) containing 4 mM EDTA and 0.05 ml of 1 mM reduced glutathione is added 0.1 ml of a cumene hydroperoxide solution with a predetermined concentration of 0–6 nmol/0.1 ml, and incubation is effected at 25° C. for 30 minutes.

After completion of the enzymatic reaction. 0.2 ml of 80 mM aqueous solution of N-ethylmaleimide is added and the reaction mixture is stirred for 10 minutes, thereby blocking the SH groups of the unreacted reduced glutathione. Then, in order to convert the oxidized glutathione produced in this enzymatic reaction to a fluorescent substance, 2.5 ml of 0.1N sodium hydroxide is added to reduce the system alkaline and, after adding 0.1 ml of 75 mM o-phthalaldehyde solution, the reaction is effected at room temperature for 30 minutes. The fluorescence of the resulting reaction mixture is measured at an exciting wavelength of 350 nm and a measuring wavelength of 420 nm using a fluorophotometer (Aminco Model SPF-125), to prepare a calibration curve.

The relationship between the amount of cumene hydroperoxide (abscissa) and the fluorescent intensity (ordinate) is given in FIG. 1.

EXAMPLE 5

To a mixed solution consisting of 0.1 ml of a solution containing 20.8 unit/ml glutathione peroxidase enzyme obtained in Example 1, 0.5 ml of 100 mM phosphate buffer (pH 6.0) containing 4 mM EDTA and 0.05 ml of 1 mM reduced glutathione is added 0.1–0.3 ml of standard serum, and incubation is effected at 25° C. for 30 minutes.

After completion of the reaction, 0.2 ml of 10% metaphosphoric acid solution is added and the reaction mixture is stirred for 10 minutes. After removing the precipitated proteins by centrifugal separation (3,000 rpm, 15 minutes), 0.3 ml of the supernatant is recovered, 0.2 ml of 80 mM aqueous solution of N-ethylmaleimide is added thereto, and the resultant mixture is stirred for 10 minutes. To the reaction mixture are added 2.5 ml of 0.1N sodium hydroxide and further, 0.1 ml of 75 mM o-phthaladehyde solution, and the reaction is effected at room temperature for 30 minutes.

The fluorescence of the resulting reaction mixture is measured at an exciting wavelength of 350 nm and a measuring wavelength of 420 nm using Aminco SPF-125 spectrofluorometer.

Figure 2:
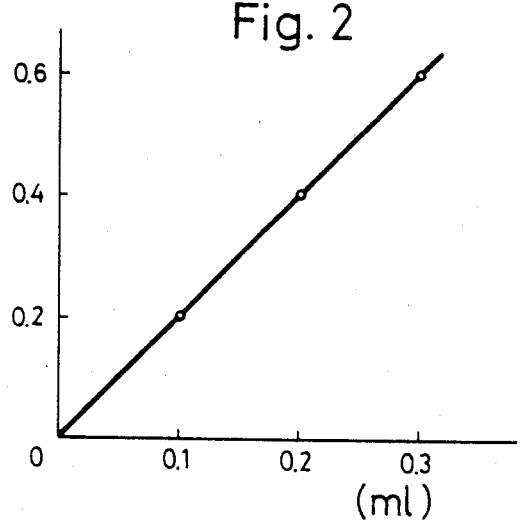

The relationship between the amount of serum tested (abscissa) and the fluorescent intensity (ordinate) is given in FIG. 2.

The calibration curve is prepared using 0-6 nmol of oxidized glutathione to determine the amount of lipid peroxide contained in the serum.

Figure 3:
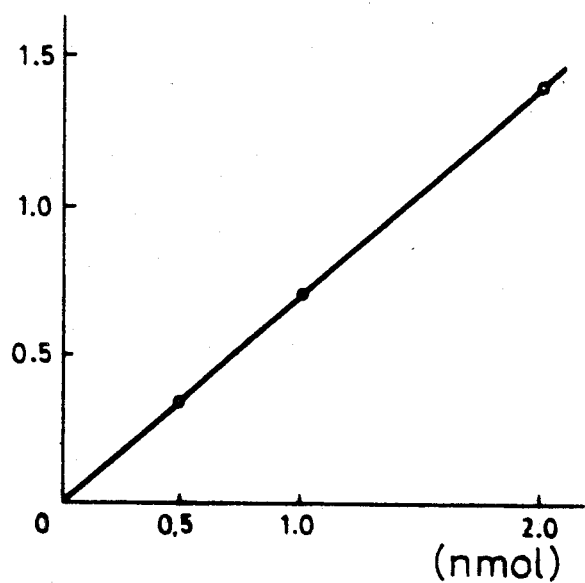

The relationship between the amount of oxidized glutathione (abscissa) and the fluorescent intensity (ordinate) is given in FIG. 3.

The determination for the amount of a lipid peroxide in the five standard serum samples (0.1 ml) is explained, taking serum No. 1 as representative.

(1) The value of fluorescent intensity of the obtained fluorescent substance, as measured by Aminco SPF-125 spectrofluorometer, is 0.2.

(2) This value, 0.2 (ordinate) corresponds to 0.2 n mole of oxidized glutathione (abscissa) in FIG. 3.

On the other hand, lipid peroxide forms an equimolecular amount of oxidized glutathione, as apparent from the aforesaid enzymatic reaction formula on page 4.

(3) Therefore, the amount of a lipid peroxide in 0.1 ml of serum is 0.28 n mole. It is concluded that 28 n moles of a lipid peroxide are contained in 1 ml of serum.

The amount of a lipid peroxide in serum sample Nos. 2 to 5 is determined in a similar manner to serum sample No. 1. The results are shown in Table 1.

TABLE 1

| Serum sample No. | The fluorescent intensity | The amount of lipid peroxide (nmol/ml) |
|---|---|---|
| 1 | 0.20 | 2.8 |
| 2 | 0.19 | 2.7 |
| 3 | 0.24 | 3.5 |
| 4 | 0.10 | 1.5 |
| 5 | 0.28 | 4.0 |

The amount of a lipid peroxide in normal human serum is about 3 n moles/ml, as reported in T. Suematsu et al., Clinica Chimica Acta, 79, 267-270 (1977).

It is found that the amount of a lipid peroxide in each of five serum samples is nearly equal to that reported in the above reference.

What is claimed is:

1. A process for the production of glutathione peroxidase which comprises culturing a microorganism capable of producing glutathione peroxides and selected from the group consisting of the species *Mucor hiemalis*, *Mucor circinelloides* and *Mucor rouxianus* in a culture medium, producing and accumulating glutathione peroxidase in the culture liquor and recovering the same therefrom.

2. A process for the production of glutathione peroxidase which comprises culturing a microorganism capable of producing glutathione peroxidase and selected from the group consisting of *Mucor hiemalis* YR-0929 (FERM BP-50), *Mucor circinelloids* ATCC 15242 and *Mucor rouxianus* YR-0319 (FERM BP-51) in a culture medium, producing and accumulating glutathione peroxidase in the culture liquor and recovering the same therefrom.

3. A method for the determination of lipid peroxide which comprises adding reduced glutathione to a sample, converting reduced glutathione in an amount corresponding to a lipid peroxide in a sample by the action of glutathione peroxidase derived from a microorganism selected from the group consisting of the species *Mucor hiemalis*, *Mucor circinelloids* and *Mucor rouxianus* into oxidized glutathione, blocking unreacted reduced glutathione with an SH reagent and determining the formed oxidized glutathione.

4. A method for the determination of lipid peroxide which comprises adding reduced glutathione to a sample, converting reduced glutathione in an amount corresponding to a lipid peroxide in a sample by the action of glutathione peroxidase derived from a microorganisms selected from the group consisting of *Mucor hiemalis* YR-0929 (FERM BP-50), *Mucor circinelloides* ATCC 15242 and *Mucor rouxianus* YR-0319 (FERM BP-51) into oxidized glutathione, blocking unreacted reduced glutathione with an SH reagent and determining the formed oxidized glutathione.

5. A method of claim 4, wherein said lipid peroxide is selected from the group consisting of cumene hydroperoxide, t-butyl hydroperoxide, linolenic acid hydroperoxide, linoleic acid hydroperoxide, cholesterol hydroperoxide, arachidonic acid hydroperoxide, progesterone hydroperoxide, allopregnanolone hydroperoxide and pregnenolone hydroperoxide.

6. A method of claim 4, wherein said SH reagent is selected from the group consisting of N-ethylmaleimide, p-chloromercurybenzoate and iodoacetic acid.

7. A method of claim 4, wherein said formed oxidized glutathione is quantitatively determined by reacting the oxidized glutathione with a fluorescent reagent to obtain a fluorescent substance, which is quantitatively determined by measuring the fluorescent intensity by a fluorophotometer.

8. A method of claim 7, wherein said fluorescent reagent is o-phthalaldehyde.

* * * * *